United States Patent
Newkirk et al.

(10) Patent No.: US 11,992,600 B1
(45) Date of Patent: May 28, 2024

(54) FLUID MANAGEMENT DEVICE AND SYSTEM

(71) Applicant: James R. Newkirk Agency, Inc., Bronx, NY (US)

(72) Inventors: James Newkirk, Bronx, NY (US); Sylvan Fowles, White Plains, NY (US)

(*) Notice: Subject to any disclaimer, the term of this patent is extended or adjusted under 35 U.S.C. 154(b) by 0 days.

(21) Appl. No.: 18/088,282

(22) Filed: Dec. 23, 2022

(51) Int. Cl.
*A61M 1/00* (2006.01)
*A61M 39/10* (2006.01)

(52) U.S. Cl.
CPC .............. *A61M 1/87* (2021.05); *A61M 1/743* (2021.05); *A61M 1/86* (2021.05); *A61M 2039/1077* (2013.01)

(58) Field of Classification Search
CPC .......... A61M 1/87; A61M 1/743; A61M 1/86; A61M 2039/1077; A61M 1/84; A61M 1/77; A61M 25/00
See application file for complete search history.

(56) References Cited

U.S. PATENT DOCUMENTS

| | | | |
|---|---|---|---|
| 2,531,730 A * | 11/1950 | Henderson | A61C 17/08 433/91 |
| 2,597,966 A | 5/1952 | Adler | |
| 3,516,160 A * | 6/1970 | Leffler | A61C 17/08 433/95 |
| 4,068,664 A * | 1/1978 | Sharp | A61M 1/84 433/91 |
| 4,287,889 A * | 9/1981 | Stupar | A61M 1/7411 604/119 |
| 4,468,216 A * | 8/1984 | Muto | A61M 1/85 604/43 |
| 4,878,900 A * | 11/1989 | Sundt | A61M 1/86 433/91 |
| 5,013,300 A * | 5/1991 | Williams | A61M 1/86 433/91 |
| 5,167,622 A * | 12/1992 | Muto | A61M 16/0463 604/35 |
| 6,045,516 A | 4/2000 | Phelan | |
| 6,152,886 A * | 11/2000 | Phelan | A61M 1/7411 433/91 |
| 6,565,544 B1 | 5/2003 | Rainin | |

(Continued)

FOREIGN PATENT DOCUMENTS

| | | | | |
|---|---|---|---|---|
| EP | 3320926 A1 * | 5/2018 | ....... | A61F 13/00068 |
| GB | 2523591 A * | 9/2015 | ............. | A61B 10/02 |

*Primary Examiner* — Nicholas J. Weiss
*Assistant Examiner* — Eric Rassavong
(74) *Attorney, Agent, or Firm* — Goldstein Law Offices, P.C.

(57) ABSTRACT

A fluid management device and system for controlling fluid at a surgical site. The device includes a flexible tube, an adapter, and a porous absorption element. The flexible tube includes a distal end, a proximal end, and a length therebetween. The length extends along a longitudinal axis. The distal end includes a distal opening configured to communicate fluid between the flexible tube and a surgical site. The adapter includes a first end coupled to the proximal end of the flexible tube and a second end configured to couple to a vacuum source or a fluid source. The porous absorption element is fixably coupled to a portion of the length of the flexible tube such that the porous absorption element encloses the distal end of the tube.

21 Claims, 9 Drawing Sheets

(56) References Cited

U.S. PATENT DOCUMENTS

| | | | |
|---|---|---|---|
| 7,699,831 B2* | 4/2010 | Bengtson | A61M 27/00 604/313 |
| 9,427,504 B2* | 8/2016 | Newman, Jr. | A61M 1/76 |
| 10,507,270 B1* | 12/2019 | Sabin | A61F 13/38 |
| 10,532,136 B2* | 1/2020 | Adams | A61M 1/74 |
| 2003/0216690 A1* | 11/2003 | Foley | A61M 1/7411 604/119 |
| 2005/0273063 A1* | 12/2005 | Hoell | A61M 1/774 604/317 |
| 2009/0111068 A1* | 4/2009 | Martinez | A61C 5/40 433/81 |
| 2012/0209203 A1* | 8/2012 | Gibertoni | A61M 1/86 604/164.11 |
| 2012/0289941 A1 | 12/2012 | Salehi et al. | |
| 2014/0088529 A1 | 3/2014 | Bengtson | |
| 2014/0276625 A1* | 9/2014 | Jenkins | A61M 1/77 604/514 |
| 2014/0276627 A1* | 9/2014 | Jenkins | A61F 13/38 604/514 |
| 2015/0231313 A1* | 8/2015 | O'Keefe | A61M 25/00 604/266 |
| 2015/0238747 A1* | 8/2015 | Russo | A61M 39/1011 604/533 |
| 2015/0359950 A1 | 12/2015 | Salehi | |
| 2016/0375180 A1* | 12/2016 | Anzai | A61L 33/0094 424/423 |
| 2017/0079756 A1 | 3/2017 | Velky | |
| 2017/0157306 A1 | 6/2017 | Voeller et al. | |
| 2018/0193120 A1 | 7/2018 | Asum | |
| 2020/0138417 A1* | 5/2020 | Abrahams | A61B 10/025 |
| 2020/0398008 A1 | 12/2020 | Kemp | |
| 2021/0128869 A1* | 5/2021 | Davis | A61M 1/77 |
| 2021/0268155 A1 | 9/2021 | Burke et al. | |
| 2021/0393907 A1* | 12/2021 | Ahmed | A61M 16/0463 |
| 2021/0393908 A1 | 12/2021 | McLain | |

* cited by examiner

FLUID MANAGEMENT DEVICE AND SYSTEM

TECHNICAL FIELD

The present disclosure relates generally to medical devices for fluid management. More particularly, the present disclosure relates to a medical device for aspirating and absorbing fluid during surgical procedures.

BACKGROUND

Minimally invasive procedures, such as laparoscopic and endoscopic procedures, have become increasingly mainstream and are often preferred over traditional surgical techniques due to reduced pain, smaller incisions, reduced hemorrhaging, and shorter recovery time. A key feature of these techniques is the use of a long fiber optic cable system that allows viewing the target area by inserting the cable through an incision from an open, more easily accessible location.

Various surgical instruments needed for such procedures, such as cannulas, retractors, aspirators, dissectors, clamps, drains, and fluid irrigation tools, are also introduced through incisions in the same manner. Sponges, gauze, bandages, and other absorbent materials to control bleeding, expose the target surgical area, and increase visibility must be applied through the same incisions. As a result, the surgical site is often crowded with numerous hands and instruments operating within the confines of small spaces and narrow openings.

The nature of minimally invasive procedures, as well as open surgical procedures performed in narrow cavities or enclosed areas of the body, often results in poor access and visibility for the surgeon performing the procedure. Poor visibility is often compounded by bleeding and poor fluid control at the surgical site.

Inability of the surgeon to control vision at the surgical site increases a likelihood that the surgeon will work outside of his or her visual field. This increases a risk of surgical inefficiencies, poor surgical outcomes, and costly and potentially life-threatening mistakes. For example, surgical sponges and other foreign bodies may be inadvertently retained inside a patient as a result of poor visibility during surgery. This type of complication can cause a patient pain and discomfort for weeks or even months after surgery.

Accordingly, what is needed is a compact fluid management device and system that increases visibility and decreases a risk of poor surgical outcomes where surgery is performed in narrow or crowded surgical environments. Also what is needed, is a fluid management device and system that provides effective and efficient fluid control and continuous fluid aspiration during minimally-invasive and open surgeries in small or narrow areas of the body. Finally what is needed, is a fluid management device and system that is inexpensive to manufacture and easy to operate.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a fluid management device for controlling fluid at a surgical site. For example, some embodiments of the fluid management device provide continuous aspiration to clear and/or absorb fluid at the surgical site. Accordingly, the present disclosure provides a flexible tube, an adapter, and a porous absorption element.

The flexible tube includes a distal end, a proximal end, and a length therebetween. The length of the flexible tube extends along a longitudinal axis. The distal end includes a distal opening configured to communicate fluid between the flexible tube and the surgical site. The adapter includes a first end coupled to the proximal end of the flexible tube and a second end configured to couple to a vacuum source and/or a fluid source. The porous absorption element is fixably coupled to a portion of the length of the flexible tube such that the absorption element encloses the distal end of the tube.

In some embodiments, the porous absorption element is fixably coupled to the flexible tube via a press fit, an adhesive, stitching, and/or a mechanical bond or fastening mechanism.

In some embodiments, the fluid management device includes the vacuum source coupled to the flexible tube and configured to provide continuous aspiration from the surgical site. In certain embodiments, the adapter includes a continuous aspiration adapter, and the second end of the continuous aspiration adapter is coupled to the vacuum source.

In some embodiments, the vacuum source is coupled to the flexible tube and configured to provide intermittent aspiration from the surgical site. In these and other embodiments, the adapter is an intermittent aspiration adapter. In some embodiments, the adapter is a dual flow adapter.

In some embodiments, the fluid source is coupled to the flexible tube to deliver fluid to the surgical site. Some embodiments of the flexible tube include multiple lateral openings in the distal end of the tube to receive a flow of fluid therethrough. Some embodiments include an end manifold coupled to the distal end of the flexible tube. The end manifold includes a plurality of perforations configured to receive a flow of fluid therethrough.

In some embodiments, the porous absorption element includes cotton, felt, rayon, and/or cellulose formed into any suitable shape. For example, the shape of the porous absorption element may be selected to facilitate introduction of the fluid management device into a narrow or confined space. In some embodiments, the shape of the porous absorption element may include a rectangular prism, a dome, a cone, a triangular spear, a cube, a pyramid, an elliptical sphere, or a circular sphere, for example. In certain embodiments, the porous absorption element includes an antithrombotic material.

Another aspect of an example embodiment in the present disclosure is to provide a fluid management system for controlling fluid at a surgical site. In some embodiments, the fluid management system includes a vacuum source configured to aspirate fluid from the surgical site. In some embodiments, the vacuum source includes an aspiration tube. The fluid management system also includes an adapter coupled to the vacuum source and a fluid management device coupled to the adapter.

In some embodiments, the fluid management device includes a flexible tube and an absorption element. The flexible tube has a distal end, a proximal end, and a length therebetween. The length of the tube extends along a longitudinal axis. In some embodiments, the distal end of the tube includes a distal opening configured to communicate fluid to and from the surgical site.

In some embodiments, the absorption element is secured to a portion of the length of the tube such that the absorption element encloses the distal end of the tube. In some embodiments, an end manifold is coupled to the distal end of the flexible tube. The end manifold includes multiple perforations configured to receive a flow of fluid therethrough. In these and other embodiments, the absorption element encloses the end manifold.

Some embodiments of the fluid management system include a dual flow adapter coupled to the proximal end of the flexible tube. The dual-flow adapter includes a first branch and a second branch. In some embodiments, the aspiration tube of the vacuum source is coupled to the first branch of the dual flow adapter.

In some embodiments, the fluid management system includes a fluid source coupled to the second branch of the dual flow adapter and configured to selectively deliver fluid to the surgical site. Some embodiments of the fluid source may include a fluid-filled bag or a syringe.

The present disclosure addresses at least one of the foregoing disadvantages of the prior art. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

As discussed above, minimally invasive procedures, such as laparoscopic and endoscopic procedures, are often preferred over traditional surgical techniques due to reduced pain, smaller incisions, reduced hemorrhaging, and shorter recovery time. Such procedures, however, require introducing a long fiber optic cable system as well as various surgical instruments and sponges through small incisions. This overcrowding of surgical instruments and hands within a confined space often results in poor visibility at the surgical site.

Open surgical procedures performed in narrow or enclosed body cavities, such as neuro, cardio/thoracic, ear, nose, and throat, oral and maxillofacial, vascular, ophthalmic, general, gynecological, and orthopedic surgeries, also risk poor visibility at the surgical site. In all cases, poor visibility is often exacerbated by bleeding and poor fluid control. The present disclosure addresses these and other issues.

As used herein, the term "proximal" refers to a portion of a device which, during normal use, is nearest the user and farthest away from the patient. The term "distal" is used herein to denote a portion of a device which, during normal use, is farthest away from the user of the device and closest to the patient. The term "fluid" is used herein to refer to any liquid, suspension, substance having no fixed shape, and/or solid having a size and shape permitting it to be transported through medical tubing.

Figure 1:
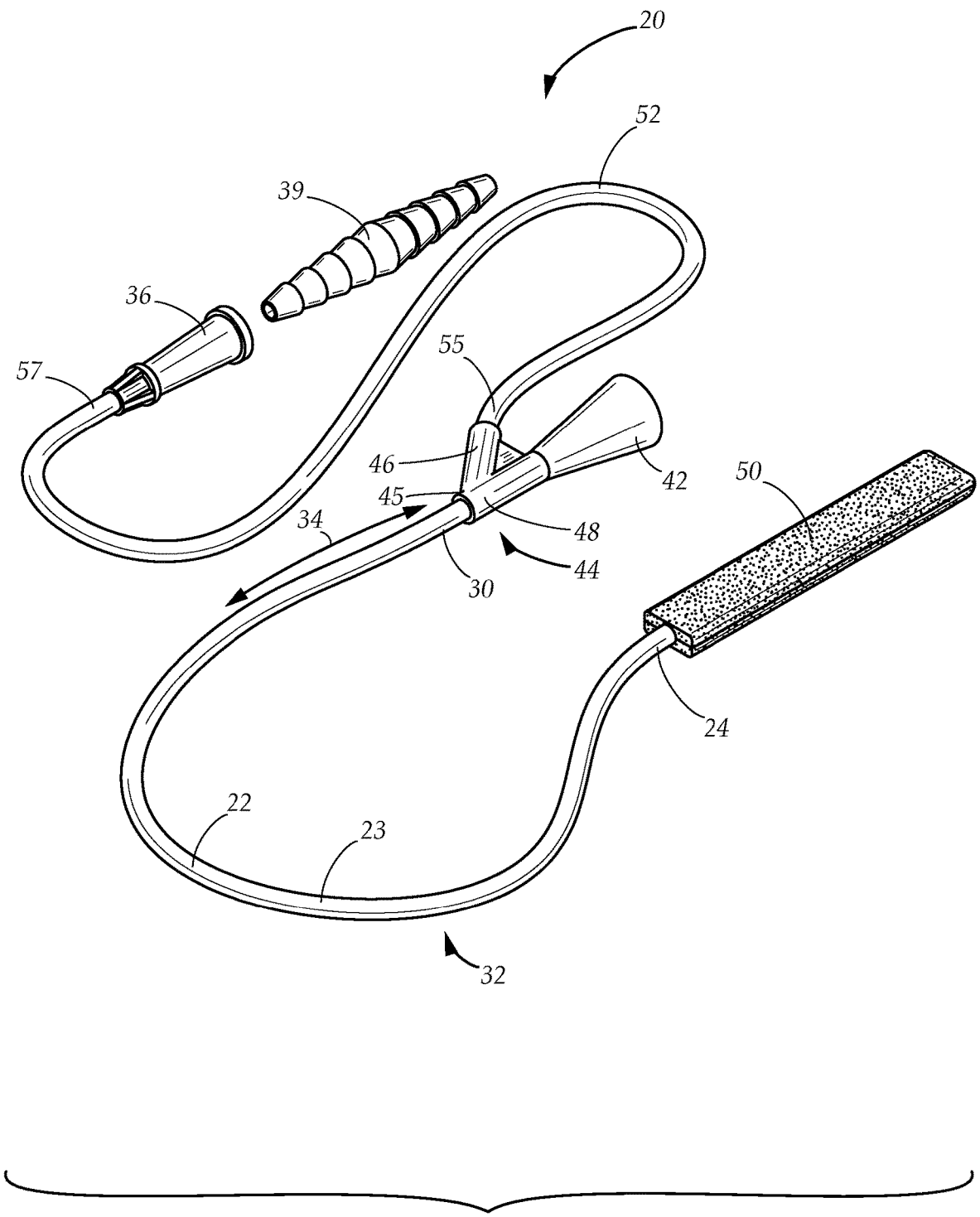
FIG. 1 is a perspective top view of a representative fluid management device in accordance with the disclosure.
Figure 2:
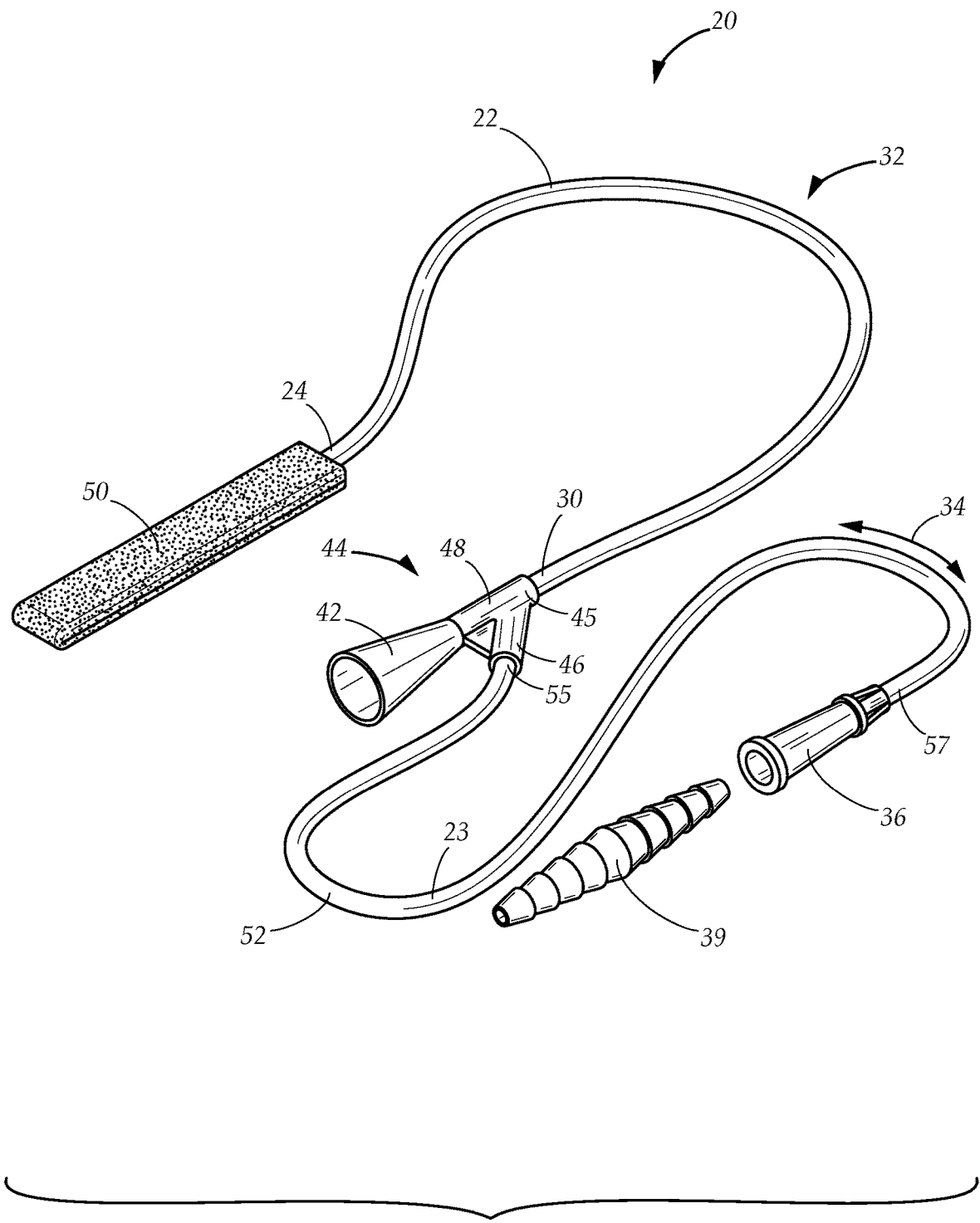
FIG. 2 is a perspective bottom view of the representative fluid management device of FIG. 1.

FIGS. 1 and 2 illustrate a fluid management device 20 for controlling blood and other fluids at a surgical site. In some embodiments, the fluid management device 20 may include a flexible tube 22 secured to a porous absorption element 50. Some embodiments of the flexible tube 22 may include one or more medical-grade, chemically-resistant materials able to withstand the high temperatures used in sterilization. In certain embodiments, the flexible tube 22 includes non-latex materials. For example, in some embodiments, the flexible tube 22 may include polyvinyl chloride (PVC), polyethylene, thermoplastic elastomers (TPE), nylon, silicone, and composites thereof.

Figure 3:
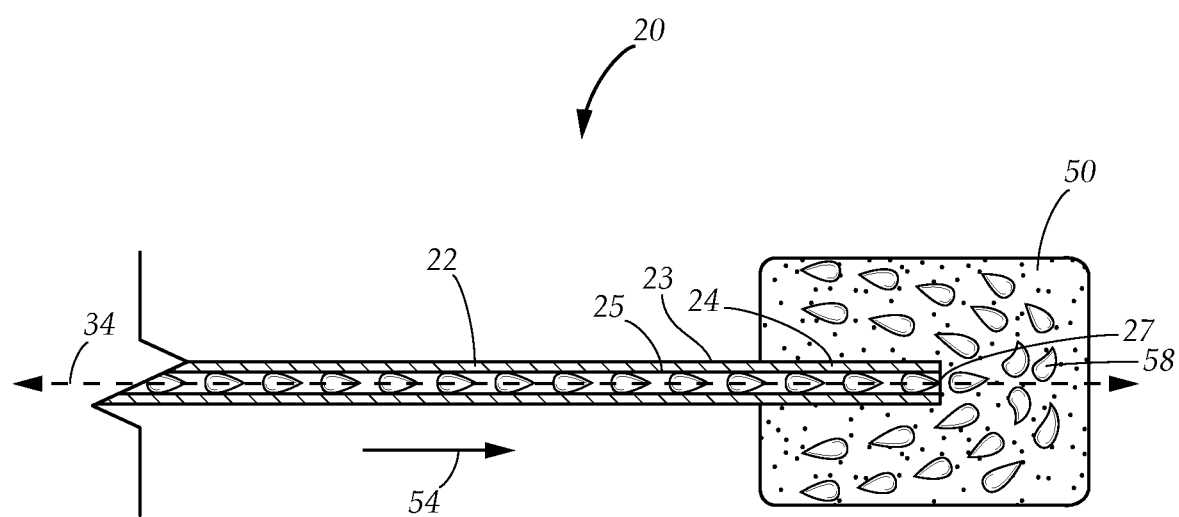
FIG. 3 is a cross-sectional diagrammatic view of a distal end of an example fluid management device, showing fluid delivery in accordance with certain embodiments.

In some embodiments, as shown in FIG. 3 and still referring to FIGS. 1 and 2, the flexible tube 22 may include an outer surface 23 and an inner lumen 25 forming a hollow cylinder along a longitudinal axis 34. In some embodiments, a length 32 of the flexible tube 22 may extend from a proximal end 30 to a distal end 24 along the longitudinal axis 34. The distal end 24 may include a distal opening 27 configured to deliver and/or aspirate fluid from the surgical site. In this manner, the cross-sectional width or diameter of the flexible tube 22 may be substantially consistent, or uniform, along the length 32 of the tube 22. Of course, the present disclosure contemplates a flexible tube 22 having any suitable shape, size, length, and/or cross-sectional width or diameter. In some embodiments, the cross-sectional width or diameter of the flexible tube 22 and/or the shape of the flexible tube 22 may vary along its length 32.

In some embodiments, the proximal end 30 of the flexible tube 22 may include a port adapter 36 configured to provide a fluid pathway between the flexible tube 22 and another tube or device, as discussed in more detail with reference to FIGS. 5A-5D below. In some embodiments, as shown in FIGS. 1 and 2, the port adapter 36 may be configured to couple to a continuous aspiration adapter 39 such that the flexible tube 22 may be coupled directly to a vacuum source, such as a central medical vacuum system or vacuum pump, for example. The vacuum source may apply a vacuum or suction force directly through the flexible tube 22 to aspirate fluid through the distal end 24.

In other embodiments, as shown, the proximal end 30 of the flexible tube 22 may include a dual-flow adapter 44 or connector, such as a Y-adapter or T-adapter. In some embodiments, the proximal end 30 of the flexible tube 22 may couple to a main port 45 of the dual-flow adapter 44. The main port 45 of the dual-flow adapter 44 may extend in a proximal direction into a first branch 46 and a second branch 48.

In some embodiments, the first branch 46 may be coupled to a distal end 55 of an aspiration tube 52. The aspiration tube 52 may include flexible medical-grade tubing similar or identical to the flexible tube 22. In some embodiments, the aspiration tube 52 may include a cross-sectional diameter greater or less than a cross-sectional diameter of the flexible tube 22. In one embodiment, the cross-sectional diameter of the aspiration tube 52 is greater than the cross-sectional diameter of the flexible tube 22.

A proximal end 57 of the aspiration tube 52 may be directly coupled to a vacuum source such that the aspiration tube 52 may apply a vacuum or suction force through the distal end 24 of the flexible tube 22 to aspirate fluid from the surgical site. In some embodiments, the proximal end 57 of the aspiration tube 52 may be directly coupled to the vacuum source via the port adapter 36 and/or the continuous aspiration adapter 39.

In these and other embodiments, the second branch 48 may be coupled to a fluid source (not shown) such that fluid may also be delivered to the surgical site through the flexible tube 22. In some embodiments, fluid may be delivered through the flexible tube 22 to flush the surgical site, to flush the flexible tube 22 following aspiration, to deliver parenteral nutrition to the patient, or for any other purpose.

In some embodiments, the second branch 48 may be coupled directly to the fluid source, such as a syringe. In other embodiments, an adapter (not shown) may couple the second branch 48 to the fluid source. In still other embodiments, as depicted in FIG. 5D for example, the second branch 48 may be coupled to a distal end 59 of a fluid tube 53 extending from the fluid source, such as a fluid-filled bag or other container. In these and other embodiments, the fluid source and/or flexible tube 22 may be configured to deliver a fluid such as saline, medicaments, and/or parenteral nutrition to the surgical site through the flexible tube 22.

Still referring to FIGS. 1 and 2, in some embodiments, the dual-flow adapter 44 may be coupled to a valve 42 or port to provide intermittent fluid aspiration via the flexible tube 22 and/or aspiration tube 52. In some embodiments, as shown in FIG. 5C, the valve 42 or port may include a chimney valve that increases in diameter from a first end 31 to a middle portion 35, and decreases from the middle portion 35 towards a second end 33. As shown in FIG. 5C, in some embodiments, the first end 31 of the chimney valve may be directly coupled to the flexible tube 22. In other embodiments, as shown in FIG. 5D, the first end 31 may be connected to the first branch 46 via an aspiration tube 52, for example. The second end 33 may define a larger opening configured to provide control of a suction force.

Figure 8:
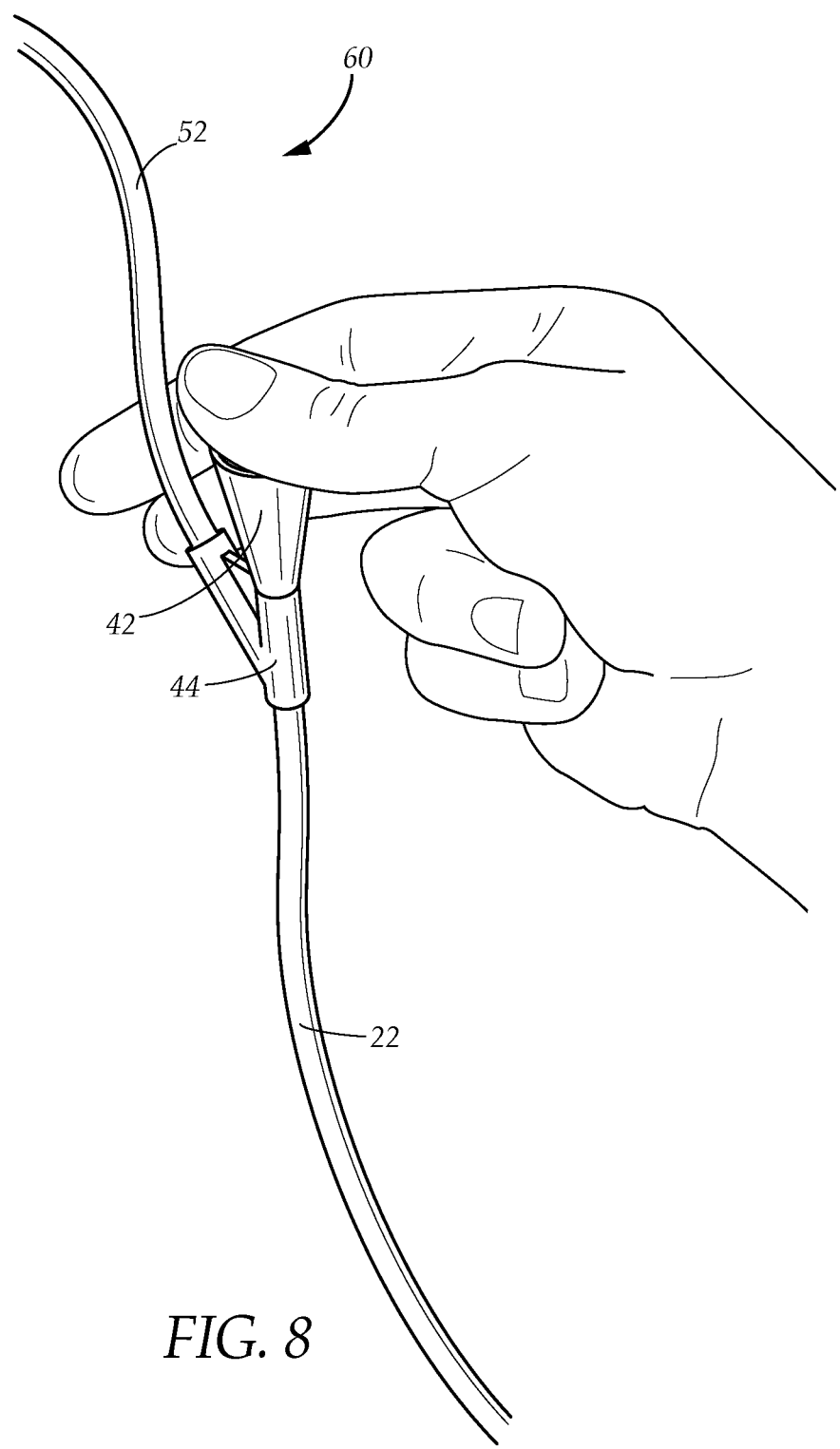
FIG. 8 is a perspective view of a portion of an example fluid management device showing operation of a valve in accordance with the disclosure.

As depicted in more detail in FIG. 8 and still referring to FIG. 5D, a user may selectively block a portion or the entirety of a valve 42 or chimney valve with a finger or thumb to control fluid aspiration. Selectively blocking the valve 42 in this manner may close the fluid path to provide a suction force at the distal opening 27 (not shown) of the flexible tube 22. Similarly, selectively occluding a portion of the valve 42 may create a reduced suction force at the distal opening 27 (not shown) of the flexible tube 22. Some embodiments of the valve 42 may thus enable the user to control both the frequency of intermittent fluid aspiration and the strength of the suction force applied through the flexible tube 22.

Some embodiments of the fluid management device 20 may include a porous absorption element 50 coupled to the distal end 24 of the flexible tube 22. In some embodiments, the porous absorption element 50 may be fixably coupled to the flexible tube 22 via an adhesive, stitching, and/or a mechanical bond or fastening mechanism. For example, in certain embodiments, the distal end 24 may include one or more mechanical features integrated into or coupled to its outer surface 23. Such mechanical features may include, for example, protrusions, ridges, grooves, recesses, openings, threads, grommets, textures, a combination thereof, and/or any other suitable features to secure at least a portion of the porous absorption element 50 to the flexible tube 22. Some embodiments may include one or more mechanical devices such as screws, rivets, staples, elastics, stitches, or other suitable mechanical fastening mechanism to secure the porous absorption element 50 to the flexible tube 22. Some embodiments of the porous absorption element 50 may include corresponding features configured to engage the mechanical features or devices of the flexible tube 22. In some embodiments, the porous absorption element 50 may include a corresponding mechanical device or feature integrated into or coupled to an inside surface of its proximal end.

In some embodiments, the porous absorption element 50 may include one or more porous, absorbent materials such as cotton, felt, rayon, and/or cellulose configured to wick and/or absorb fluid from the surgical site. In some embodiments, the porous absorption element 50 may include a sponge. In some embodiments, the porous absorption element 50 may include more than one layer. The layers may be stitched together via any suitable medical-grade synthetic or non-synthetic material or thread. In some embodiments, the porous absorption element 50 may include one or more Cottonoid® pads, paddies, surgical sponges, a combination thereof, and/or any other suitable material or element.

In certain embodiments, the porous absorption element 50 may be formed to extend along at least a portion of the length 32 of the flexible tube 22. In some embodiments, as discussed in more detail with reference to FIGS. 4A-4E, the porous absorption element 50 may be formed into an elongate three-dimensional regular or irregular shape. In some embodiments, the porous absorption element 50 may include a string, tab, indentation, or other removal device integrated into or coupled thereto to facilitate removal of the porous absorption element 50 from the flexible tube 22 and/or surgical site if needed. In certain embodiments, the porous absorption element 50 may be oriented and/or secured around the flexible tube 22 such that the porous absorption element 50 may be selectively unfolded to expose a greater surface area as desired.

Referring now to FIG. 3, in some embodiments, the distal opening 27 of the flexible tube 22 may be configured to receive a flow of fluid 58 in a distal 54 or proximal direction through the flexible tube 22. The direction of fluid flow 58 through the flexible tube 22 may be determined by the device coupled to its proximal end 30 (not shown). A vacuum source coupled to the proximal end 30 (not shown) may aspirate fluid from the surgical site, while a fluid source coupled to the proximal end 30 (not shown) may deliver fluid to the surgical site.

In some embodiments, the porous absorption element 50 may be formed to encapsulate the distal end 24 of the flexible tube 22 and enclose the distal opening 27. In operation, in some embodiments, a vacuum force applied through the flexible tube 22 may pull fluid in a proximal direction through the porous absorption element 50 and distal opening 27 and into the flexible tube 22. The porous absorption element 50 may thus wick and/or filter fluid from the surgical site before it is received into the flexible tube 22. In some embodiments, the porous absorption element 50 may simultaneously absorb fluid from the surgical site while the flexible tube 22 draws fluid therethrough.

In other embodiments, as shown, operation of the fluid management device 20 may cause fluid to flow in a distal direction 54 to exit the flexible tube 22 through the distal opening 27. In some embodiments, the fluid may be absorbed and/or filtered by the porous absorption element 50 prior to delivery at the surgical site. In certain embodiments, one or more medications or other additives may impregnate or be applied to the porous absorption element 50 to provide additional antibacterial, hemostatic, or other benefits. In one embodiment, for example, an antithrombotic or antithrombogenic material such as heparin, for example, may be integrated into the porous absorption element 50 such that fluid flow therethrough may cause the antithrombotic material to leech out of the porous absorption element 50 at the surgical site.

Figures 4A, 4B, 4C, 4D, 4E:
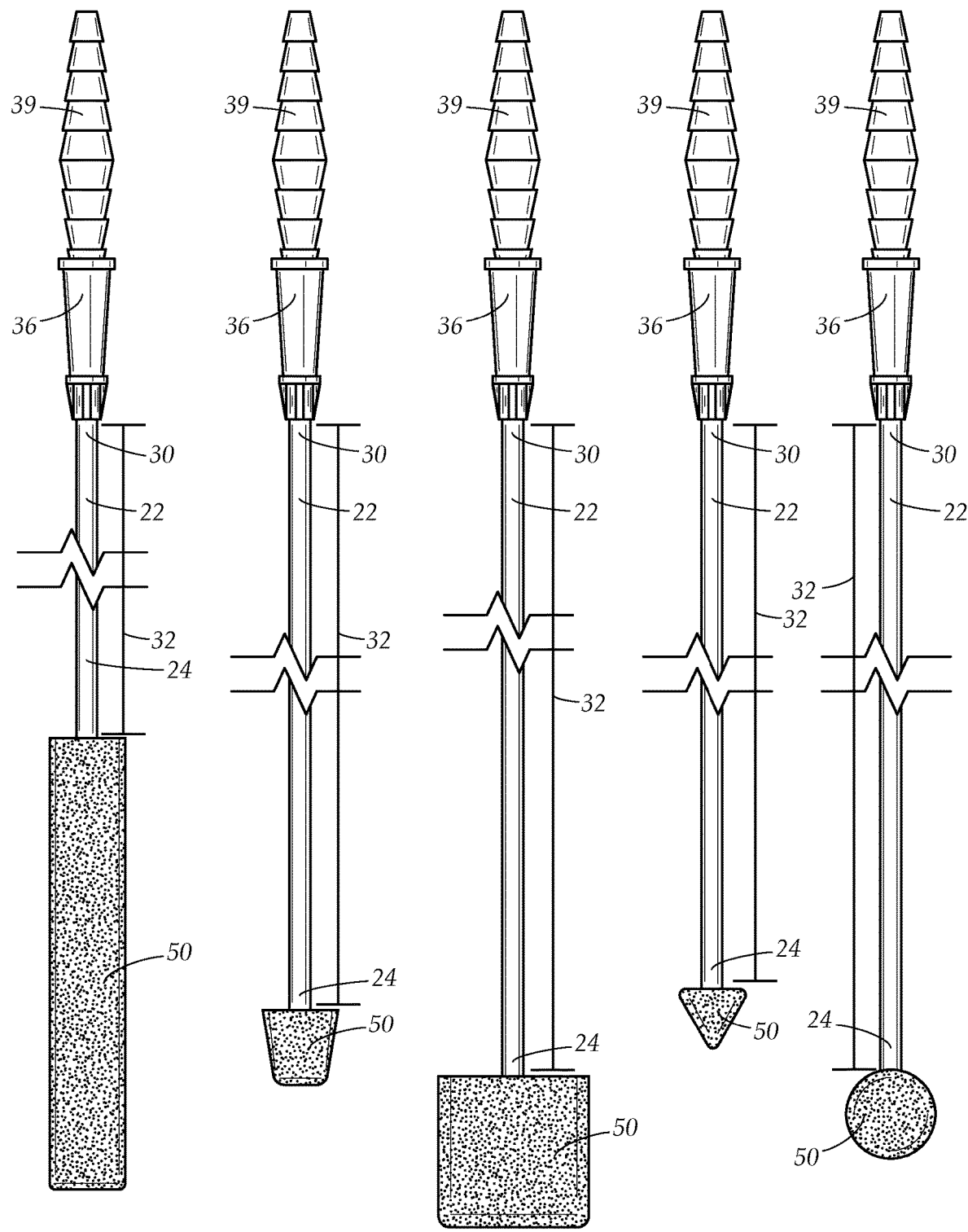
FIG. 4A is a top perspective view of a distal end of an example embodiment of a fluid management device having a rectangular prism-shaped absorption element.
FIG. 4B is a top perspective view of a distal end of an example embodiment of a fluid management device having a dome-shaped absorption element.
FIG. 4C is a top perspective view of a distal end of an example embodiment of a fluid management device having a cube-shaped absorption element.
FIG. 4D is a top perspective view of a distal end of an example embodiment of a fluid management device having a triangular spear-shaped absorption element.
FIG. 4E is a top perspective view of a distal end of an example embodiment of a fluid management device having a circular sphere-shaped absorption element.

Referring to FIGS. 4A-4E, in some embodiments, the porous absorption element 50 may be formed into any suitable shape. For example, the shape of the porous absorption element may be selected to facilitate introduction of the flexible tube 22 into a small, narrow, and/or confined surgical site. In some embodiments, for example, the shape of the porous absorption element 50 may include a rectangular prism as shown in FIG. 4A, a dome as shown in FIG. 4B, a cone, a cube as shown in FIG. 4C, a triangular spear as shown in FIG. 4D, a pyramid, an elliptical sphere, or a circular sphere as shown in FIG. 4E.

In some embodiments, as shown in FIG. 4A, the shape of the porous absorption element 50 may extend along at least a portion of the length 32 of the flexible tube 22. In other embodiments, as shown in FIGS. 4D and 4E, for example, the shape of the porous absorption element 50 may require that it is coupled closer to the distal end 24 and distal opening 27 (not shown). In any case, the proximal end 30 of the flexible tube 22 may include a port adapter 36, a continuous aspiration adapter 39, an intermittent aspiration adapter 40 (not shown), and/or other suitable adapter.

Figure 5A:
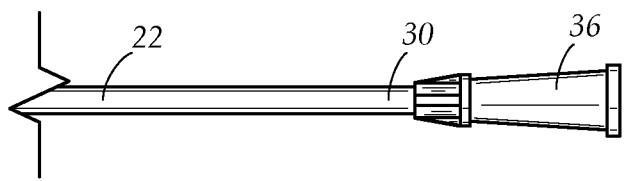
FIG. 5A is a perspective view of a proximal end of an example embodiment of a fluid management device in accordance with the disclosure.
Figure 5B:
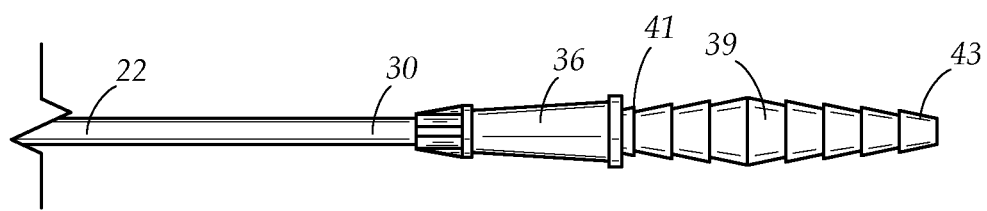
FIG. 5B is a perspective view of a proximal end of an example embodiment of a fluid management device having an adapter in accordance with the disclosure.
Figure 5C:
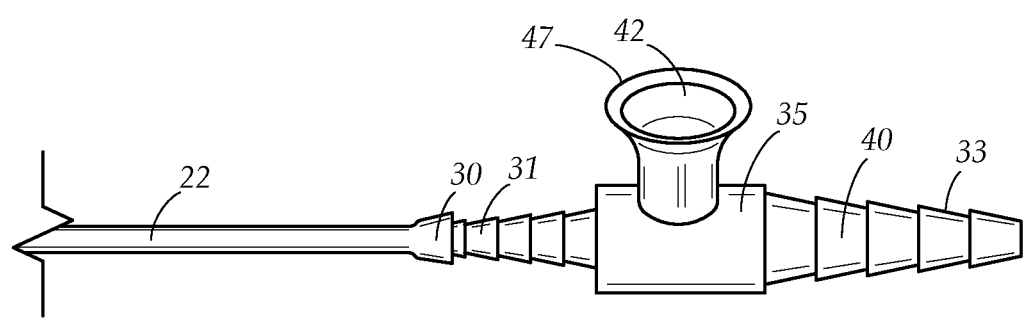
FIG. 5C is a perspective view of a proximal end of an example embodiment of a fluid management device having a valve in accordance with some embodiments.
Figure 5D:
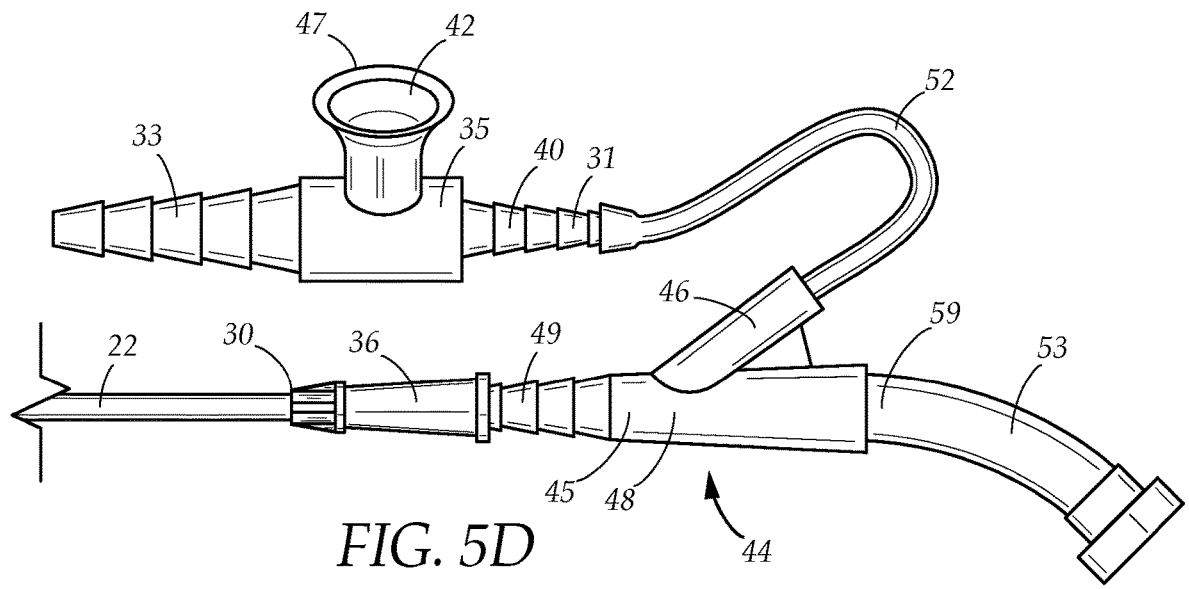
FIG. 5D is a perspective view of a proximal end of an example embodiment of a fluid management device having a dual-flow connector and valve in accordance with the disclosure.

Referring now to FIGS. 5A-5D, in some embodiments, the flexible tube 22 may be configured to apply a vacuum force therethrough. In certain embodiments, as shown in FIG. 5A, the proximal end 30 of the flexible tube 22 may include a port adapter 36 or fitting to couple the flexible tube 22 directly to the vacuum source. In other embodiments, the proximal end 30 of the flexible tube 22 may include a port adapter 36 to couple the flexible tube 22 to a continuous aspiration adapter 39, as shown in FIG. 5B. In some embodiments, the continuous aspiration adapter 39 may include a lightweight, vinyl plastic with varying thread sizes to fit various devices and tubes. In this manner, the continuous aspiration adapter 39 may be implemented with flexible tubes 22 and aspiration tubes 52 having various sizes and diameters. As shown, in some embodiments, the continuous aspiration adapter 39 may gradually increase in diameter from each end 41, 43 towards its center. In this manner, a cross-sectional diameter of the continuous aspiration adapter 39 may be greatest at its middle and may gradually taper towards either end 41, 43.

In other embodiments, as shown in FIG. 5C, the proximal end 30 of the flexible tube 22 may include an intermittent aspiration adapter 40 having a valve 42, port, or other similar feature or device to provide a controlled intermittent vacuum force through the flexible tube 22. Similar to the continuous aspiration adapter 39, some embodiments of the intermittent aspiration adapter 40 may also include a lightweight, vinyl or plastic. In some embodiments, the intermittent aspiration adapter 40 may include varying thread sizes to fit various devices and tubes 22, 52. Similar to the continuous aspiration adapter 39, the intermittent aspiration adapter 40 may include an elongate shape having a cross-sectional diameter that gradually increases from either end 31, 33 towards a middle section 35. In some embodiments, the middle section 35 may include a cylindrical shape having a uniform or substantially uniform cross-sectional diameter.

In certain embodiments, the cross-sectional diameter of the intermittent aspiration adapter 40 may taper from either edge of the middle section 35 towards a respective end 31, 33. In some embodiments, the cross-sectional diameter of the intermittent aspiration adapter 40 at a position immediately adjacent to the middle section 35 may be smaller on one side than the other. For example, as shown, some embodiments of the intermittent aspiration adapter 40 may include a cross-sectional diameter that gradually tapers in dimension from the middle section 35 towards the second end 33 of the intermittent aspiration adapter 40. On the other hand, in some embodiments, the cross-sectional diameter may decrease immediately at an opposite edge of the middle section 35 and may continue to decrease towards the first end 31 of the intermittent aspiration adapter 40. In addition, in some embodiments, the first end 31 may include a length shorter than the second end 33. In these and other embodiments, the smaller dimensions in diameter and length of the first end 31 may facilitate connection to the flexible tube 22 or aspiration tube 52, while the larger dimensions in diameter and length of the second end 33 may facilitate connection to a vacuum source, for example.

In some embodiments, the middle section 35 of the intermittent aspiration adapter 40 may include a valve 42 or other port feature in fluid communication with an interior of the middle section 35 of the intermittent aspiration adapter 40 and extending orthogonally relative thereto. In certain embodiments, the valve 42 may include a cylindrical shape that includes a flare 47, or lip, at its distal end. In some embodiments, the flare 47 may define an opening that may be selectively occluded to provide intermittent aspiration. In other embodiments, the flare may be configured to connect to another tube or fluid source. In some embodiments, the valve 42 may be a chimney valve.

In still other embodiments, as show in FIG. 5D, the proximal end 30 of the flexible tube 22 may be coupled to a dual-flow adapter 44. As shown, an aspiration tube 52 may be coupled to the first branch 46 of the dual-flow adapter 44 and may include an intermittent aspiration adapter 40 attached to its proximal end. In certain embodiments, the second branch 48 of the dual-flow adapter 44 may be coupled to a fluid delivery tube 53 extending from a fluid source, such as a saline bag or other fluid-filled delivery bag or container.

As shown, in some embodiments, the second branch 48 of the dual-flow adapter 44 may include a greater cross-sectional diameter than the first branch 46 of the dual-flow adapter 44. In some embodiments, this feature may permit the second branch 48 of the dual-flow adapter 44 to accommodate a greater volume of fluid flow therethrough relative to the first branch 46 of the dual-flow adapter 44. Further, in some embodiments, the second branch 48 may include an adapter extension portion 49 having varying thread sizes to accommodate connection with various sizes of ports or tubes. In some embodiments, the adapter extension portion 49 may be coupled to the main port 45 or branch 48 of the dual-flow adapter 44. In other embodiments, the adapter extension portion 49 may be molded or otherwise integrated with the dual-flow adapter 44.

Figure 5E:
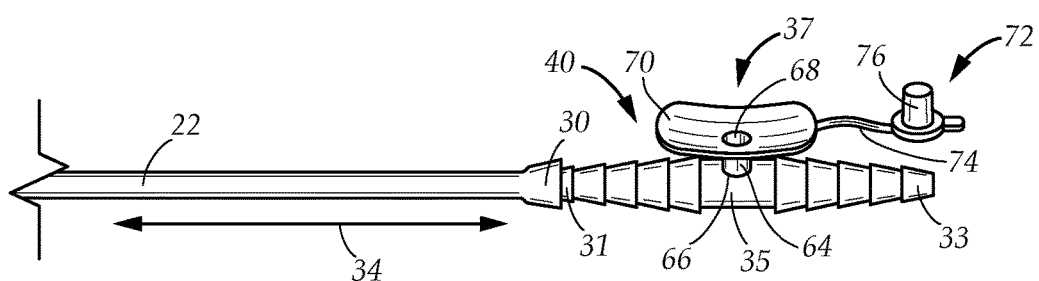
FIG. 5E is a perspective view of a representative intermittent aspiration adapter having a nipple closure in accordance with certain embodiments.

Referring now to FIG. 5E, in some embodiments, the intermittent aspiration adapter 40 may extend from the first end 31 to the second end 33 along the longitudinal axis 34. The intermittent aspiration adapter 40 may include a middle section 35 disposed between the first end 31 and the second end 33. In some embodiments, the middle section 35 may include an aperture 66 extending from an interior to an exterior of the intermittent aspiration adapter 40. Some embodiments of the intermittent aspiration adapter 40 may include a funnel valve 37 extending in a transverse direction from the aperture 36 such that the funnel valve 37 is in fluid communication with the intermittent aspiration adapter 40.

In some embodiments, the funnel valve 37 may include a narrow neck portion 64 extending into a larger cone portion 70. In some embodiments, the narrow neck portion 64 may include a cylindrical tube where the aperture 66 of the middle section 35 defines a base of the tube. In these and other embodiments, the narrow neck portion 64 may include a top edge defining an opening 68 in the cone portion 70. In this manner, the neck portion 64 may form a fluid pathway between the cone portion 70 and the intermittent aspiration adapter 40.

In some embodiments, the cone portion 70 may include an oblong cup shape extending parallel to the longitudinal axis 34. In some embodiments, a top opening 72 of the cone portion 70 may include a shape such as a rectangle, a square, a circle, or any other suitable shape. In other embodiments, the cone portion 70 may include a regular cone shape, an inverted dome shape, an inverted pyramid shape, or any other suitable three-dimensional shape having a greatest diameter or cross-sectional area at the top opening 72 and narrowing to a smallest diameter or cross-sectional area at the opening 68.

In some embodiments, a nipple closure 72 or other lid or closure device may be coupled to the funnel valve 37 to selectively occlude and/or seal the opening 68. For example, in some embodiments, the nipple closure 72 may include a strap 74 coupled to the cone portion 70 or neck portion 64 of the funnel valve 37. In some embodiments, the strap 74 may be flexible and may include a material such as silicone, rubber, or other suitable material. In some embodiments, the strap 74, nipple closure 72, and/or funnel valve 37 may be monolithically formed as a single unit.

In some embodiments, the nipple closure 72 may include a nipple 76 adapted to be received into the neck portion 64 of the funnel valve 37 and to selectively close and/or seal the opening 68 of the funnel valve 37 via a press fit. In some embodiments, inserting the nipple 76 into the neck portion 64 may create a suction force on the nipple closure 72 to seal the opening 68 and maintain the nipple closure 72 in a closed position relative to the opening 68. The nipple 76 may be retracted from the opening 68 to remove the occlusion and/or break the seal. In some embodiments, the nipple 76 may include a shape having dimensions equal to or less than an inner length and/or width or diameter of the neck portion 64. For example, as shown, the nipple 76 may include a cylinder shape having dimensions equal to or less than an inner length and diameter of the cylindrical neck portion 64.

In some embodiments, actuating the nipple closure 72 to occlude the opening 68 in this manner may create a vacuum force that extends through the flexible tube 22. Similarly, removing the nipple closure 72 from the opening 68 may extinguish the vacuum force. In this manner, the intermittent aspiration adapter 40 may apply intermittent aspiration through the flexible tube 22.

Figure 6:
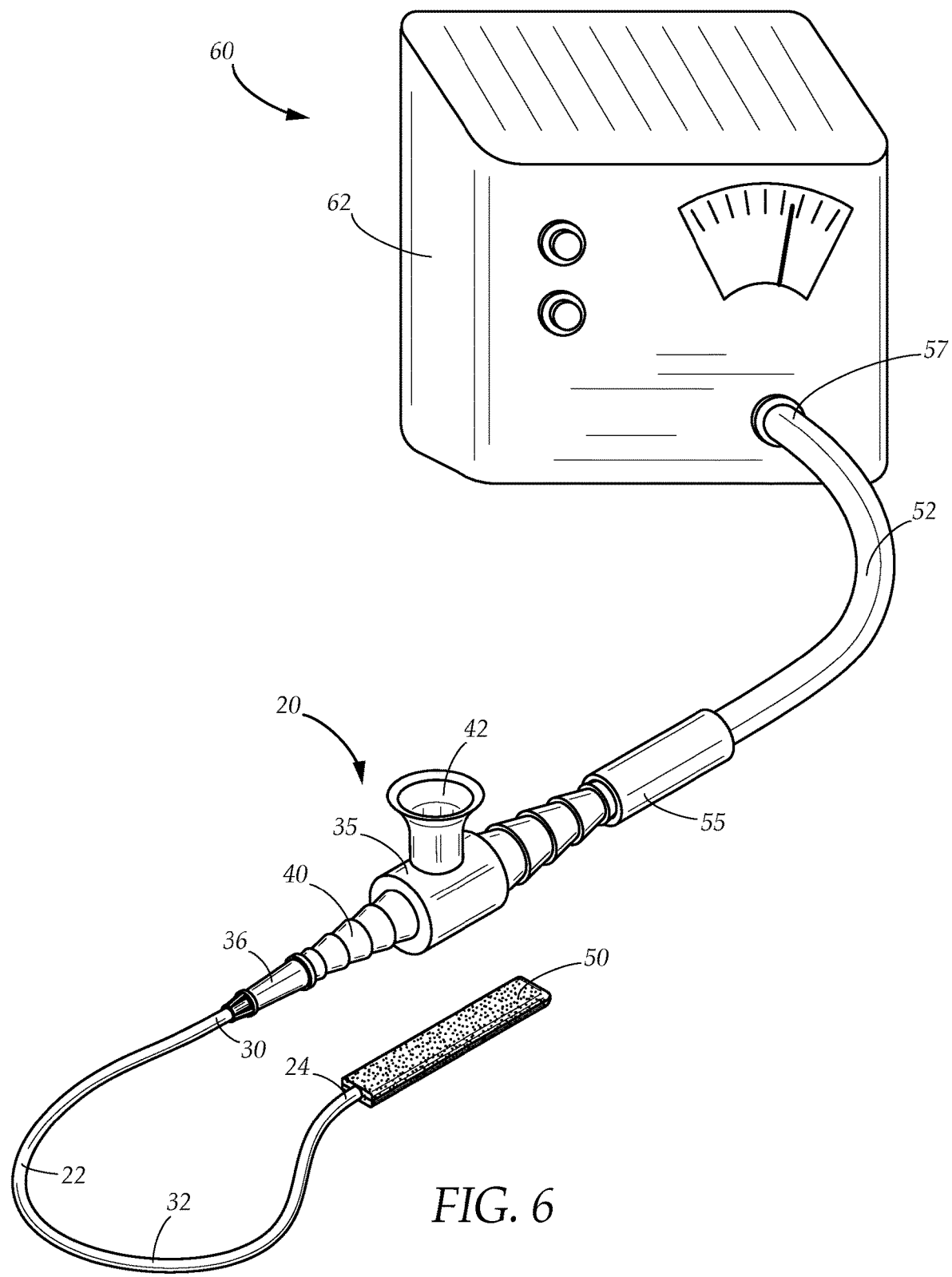
FIG. 6 is a perspective view of a fluid management system in accordance with some embodiments.

Referring now to FIG. 6, some embodiments provide a fluid management system 60 for controlling fluid at a surgical site. In some embodiments, the fluid management system 60 may include a vacuum source 62 having an aspiration tube 52. In some embodiments, the vacuum source 62 may include a central vacuum system or vacuum pump, such as those provided in hospitals, surgical centers, doctor's office, and the like. In some embodiments, the vacuum source 62 may include an internal fluid receptacle (not shown) to collect fluid aspirated from the surgical site. In other embodiments, a separate fluid receptacle (not shown) may be coupled to or in fluid communication with the flexible tube 22.

A distal end 55 of the aspiration tube 52 may be coupled to the fluid management device 20, as discussed in detail above with reference to FIGS. 1, 2, and 5A-5D. In some embodiments, the distal end 55 of the aspiration tube 52 may include an intermittent aspiration adapter 40. As shown, the intermittent aspiration adapter 40 may include a valve 42 such as a chimney valve or other suitable valve or port extending orthogonally from a middle section 35 thereof to control the frequency and/or strength of fluid aspiration, as discussed above with reference to FIG. 1.

In some embodiments, the fluid management device 20 may include a flexible tube 22 having a distal end 24, a proximal end 30, and a length 32 therebetween. The length 32 may extend along a longitudinal axis. In some embodiments, a port adapter 36 may couple the proximal end 30 to an end of the intermittent aspiration adapter 40. The distal end 24 may include a distal opening (not shown) disposed within the porous absorption element 50 to provide continuous fluid aspiration to and from the surgical site.

In some embodiments, the absorption element 50 may be secured to a portion of the length 32 of the flexible tube 22 such that the absorption element 50 encloses the distal end 24. In some embodiments, at least a portion of the absorption element 50 may be formed around the flexible tube 22, or a portion of the flexible tube 22 may be inserted into and retained by the absorption element 50. In this manner, the porous absorption element 50 may absorb fluid while the flexible tube 22 simultaneously provides continuous fluid aspiration at the surgical site.

Figure 7A:
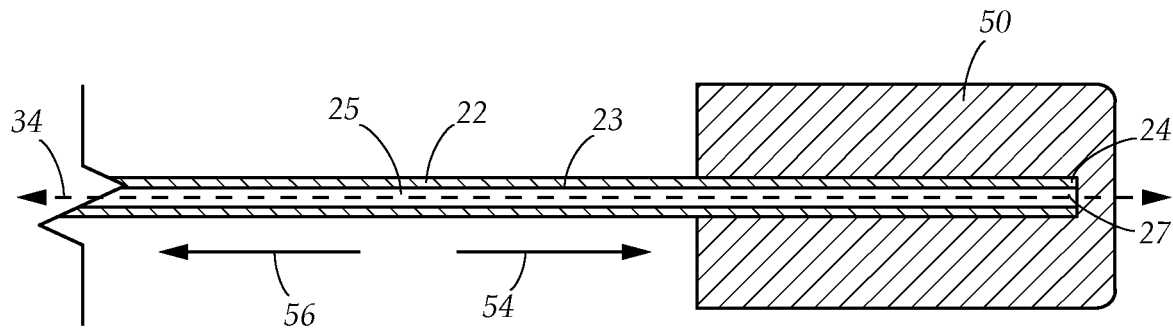
FIG. 7A is a cross-sectional diagrammatic view of a distal end of an example fluid management device having a distal opening in accordance with the disclosure.

Referring now to FIG. 7A, in some embodiments, the distal end 24 of the flexible tube 22 may include a distal opening 27 to permit a flow of fluid into and/or out of the flexible tube 22. In some embodiments, the distal opening 27 provides continuous aspiration of fluid through the flexible tube 22. In some embodiments, as shown, the porous absorption element 50 may be attached to a portion of the length 32 (not shown) of the flexible tube 22 such that the porous absorption element 50 encapsulates the distal end 24 and occludes the distal opening 27. In some embodiments, the porous absorption element 50 may be coupled to the flexible tube 22 such that it extends along the at least one-quarter of the length 32 (not shown) of the flexible tube 22 from its distal end 24. In other embodiments, the porous absorption element 50 may extend along less than one-quarter, one-eighth, or one-tenth of the length 32 (not shown) of the flexible tube 22 from its distal end 24.

In some embodiments, the porous absorption element 50 may include a sponge having a bore therethrough to receive a portion of the length 32 (not shown) of the flexible tube 22. In certain embodiments, the distal end 24 of the flexible tube 22 may extend through the sponge such that the distal opening 27 is exposed. In other embodiments, the distal opening 27 may be encapsulated or occluded by a distal portion of the sponge. In these and other embodiments, the distal opening 27 may provide continuous aspiration through the sponge.

In some embodiments, the porous absorption element 50 may include multiple layers configured to receive a distal portion of the length 32 (not shown) of the flexible tube 22 between the layers. In certain embodiments, two or more porous absorption elements 50 may be sandwiched together such that a distal portion of the flexible tube 22 may be retained between the porous absorption elements 50.

In some embodiments, a distal portion of the flexible tube 22 may be coupled directly to the porous absorption element 50. In other embodiments, the porous absorption element 50 may be coupled to itself and/or to another porous absorption element 50 to retain a distal portion of the flexible tube 22 therein via a press fit, for example.

In this manner, fluid from the surgical site may be continually or intermittently aspirated in a proximal direction 56 through the distal opening 27 and/or porous absorption element 50. In some embodiments, fluid may also be delivered in a distal direction 54 through the flexible tube 22, distal opening 27 and/or porous absorption element 50.

Figure 7B:
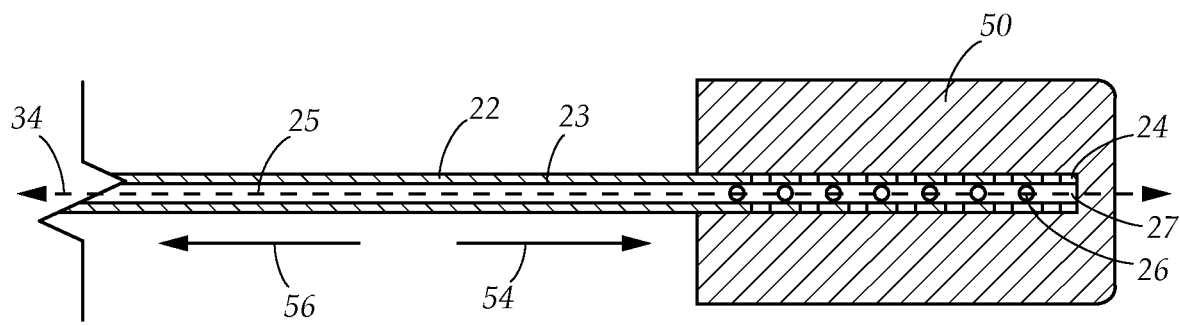
FIG. 7B is a cross-sectional diagrammatic view of a distal end of an example fluid management device showing multiple lateral openings in the flexible tube in accordance with certain embodiments.

Referring now to FIG. 7B, some embodiments of the flexible tube 22 may include one or more lateral openings 26 in the distal end 24 of the flexible tube 22 to receive a flow of fluid therethrough. One or more of the lateral openings 26 may extend through the outer surface 23 and inner lumen 25 of the flexible tube 22 in a direction transverse to the longitudinal axis 34 to transport fluid between the porous absorption element 50 and the flexible tube 22. In some embodiments, the distal opening 27 may also receive a flow of fluid from the porous absorption element 50.

In this manner, some embodiments may aspirate fluid through the porous absorption element 50 into the inner lumen 25 and may transport the fluid in a proximal direction 56 through the flexible tube 22. In other embodiments, fluid may flow through the flexible tube 22 in a distal direction 54 and may exit the flexible tube 22 through one or more of the lateral openings 26 and/or distal opening 27.

Figure 7C:
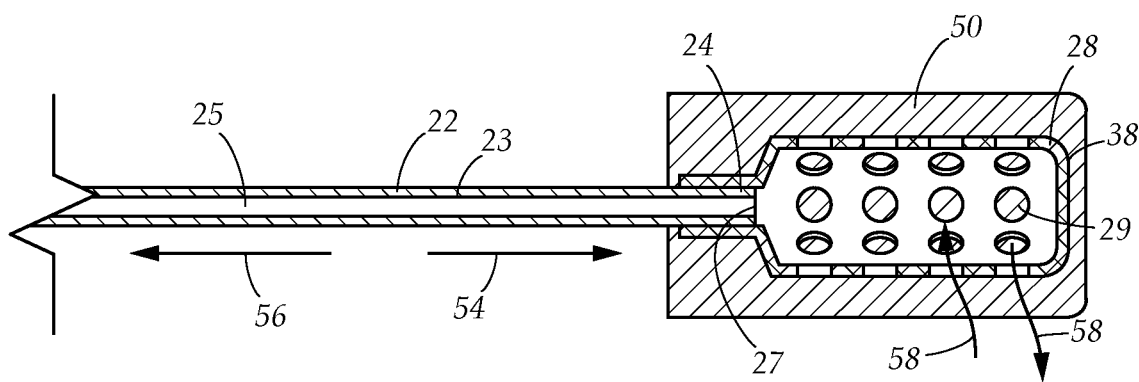
FIG. 7C is a cross-sectional diagrammatic view of a distal end of an example fluid management device having a perforated end manifold in accordance with certain embodiments.

Referring now to FIG. 7C, in some embodiments, a perforated end manifold 28 may be coupled to the distal end 24 of the flexible tube 22 via an adhesive or a press fit, for example. In other embodiments, the perforated end manifold 28 may be coupled to the flexible tube 22 via threads or another suitable mechanical feature or device.

In some embodiments, the perforated end manifold 28 may include a receptacle having an enlarged diameter and volume relative to the distal opening 27 and distal end 24 of the flexible tube 22. The perforated end manifold 28 may also include multiple openings or perforations 29 disposed in a transverse direction therethrough. In some embodiments, each opening or perforation 29 may include dimensions equal to or greater than those of the distal opening 27. In this manner, the perforated end manifold 28 may accommodate a significantly larger flow of fluid 58 into and out of the flexible tube 22. Like other embodiments, fluid may be aspirated in a proximal direction 56 through the perforated end manifold 28 and/or may be delivered in a distal direction 54 through the perforated end manifold 28 to a surgical site.

In some embodiments, the perforated end manifold 28 may obstruct the distal opening 27 of the flexible tube 22. Further, in some embodiments, the perforated end manifold 28 may include a closed distal end 38. In these and other embodiments, the perforated end manifold 28 may reduce a rate of fluid flow by preventing fluid from directly entering or directly exiting the distal end 24 of the flexible tube 22. In some embodiments, the porous absorption element 50 may encase and/or enclose the perforated end manifold 28.

Referring now to FIG. 8, some embodiments may provide a valve 42, such as a dual port valve or other port or opening, coupled to a dual-flow adapter 44. As shown, in some embodiments, the user may manipulate the valve 42 such that a finger or thumb selectively blocks at least a portion of the valve 42. In this manner, the user may control the suction force provided at the distal end 24 (not shown) of the flexible tube 22. Entirely closing the valve 42 may close the fluid path to provide a strong suction force, while selectively occluding a portion of the valve 42 may create a reduced suction force. Similarly, in some embodiments, the user may selectively open and close the valve 42 to provide intermittent aspiration through the flexible tube 22.

The description of the present disclosure has been presented for purposes of illustration and description but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

In conclusion, herein is presented a fluid management device and system for controlling fluid at a surgical site. The disclosure is illustrated by example in the drawing figures, and throughout the written description. It should be understood that numerous variations are possible, while adhering to the inventive concept. Such variations are contemplated as being a part of the present disclosure.

What is claimed is:

1. A fluid management device for controlling fluid at a surgical site, comprising:
   a flexible tube having a distal end, a proximal end, and a length therebetween, wherein the length extends along a longitudinal axis and wherein the distal end comprises a distal opening configured to communicate fluid between the flexible tube and the surgical site;
   a dual flow adapter having a main port, a first branch, and a second branch, wherein the main port is coupled to the proximal end of the flexible tube and wherein the first branch is disposed at an acute angle relative to the main port, wherein the first branch is directly coupled to a vacuum source via an aspiration tube, and wherein the second branch is coaxial with the main port and is configured to be interchangeably coupled to one of a fluid source and an intermittent aspiration adapter configured to provide intermittent fluid aspiration through the flexible tube; and
   a porous absorption element fixably coupled to a portion of the length of the flexible tube such that the porous absorption element encloses the distal end.

2. The fluid management device of claim 1, further comprising the vacuum source, wherein the vacuum source is in fluid communication with the flexible tube and configured to provide continuous aspiration from the surgical site.

3. The fluid management device of claim 2, further comprising a continuous aspiration adapter disposed between the vacuum source and the aspiration tube, wherein the continuous aspiration adapter includes an elongate body having a first end, a second end, and a center between the first end and the second end, the continuous aspiration adapter increasing in diameter from the first end and the second end toward the center such that the diameter of the continuous aspiration adapter tapers from its center toward the first end and the second end, the second end of the continuous aspiration adapter coupled to the vacuum source.

4. The fluid management device of claim 1, wherein the intermittent aspiration adapter comprises a chimney valve.

5. The fluid management device of claim 1, wherein the intermittent aspiration adapter comprises an elongate body having an interior surface for fluid communication, a first end, a second end, a middle section, and a center on the middle section, the intermittent aspiration adapter increasing in diameter from the first end and the second end toward the middle section such that the diameter of the intermittent aspiration adapter tapers from the middle section toward the first end and the second end, the middle section including a uniform cross-sectional diameter and a valve extending orthogonally outwardly therefrom, the valve in fluid communication with the interior surface and including a distal end having an opening for selectively occluding to provide a controlled intermittent vacuum force and intermittent aspiration to a surgical site.

6. The fluid management device of claim 4, wherein the intermittent aspiration adapter comprises an interior surface for fluid communication, a first end, a second end, a middle section, and a center on the middle section, the intermittent aspiration adapter extending from the first end to the second end along the longitudinal axis and increasing in diameter from the first end and the second end toward the middle section such that the diameter of the intermittent aspiration adapter tapers from the middle section toward the first end and the second end, the middle section including a uniform cross-sectional diameter and a funnel valve extending orthogonally outwardly therefrom, the funnel valve in fluid communication with the interior surface and including an opening and a nipple closure, the nipple closure including a nipple configured to selectively occlude the opening to provide a controlled intermittent vacuum force and intermittent aspiration to a surgical site.

7. The fluid management device of claim 1, wherein the second branch of the dual flow adapter includes a greater cross-sectional diameter than the first branch.

8. The fluid management device of claim 7, wherein the second branch includes an adapter extension portion tapering in diameter from the main branch towards an end of the adapter extension portion and defines varying thread sizes to accommodate connection with various ports or tubes.

9. The fluid management device of claim 1, further comprising the fluid source coupled to the second branch to deliver fluid to the surgical site through the flexible tube.

10. The fluid management device of claim 1, wherein the distal end of the flexible tube includes a plurality of lateral openings configured to receive a flow of fluid therethrough.

11. The fluid management device of claim 1, further comprising an end manifold coupled to the distal end of the flexible tube, the end manifold comprising a plurality of perforations configured to receive a flow of fluid therethrough.

12. The fluid management device of claim 1, wherein the porous absorption element comprises a shape selected from the group consisting of a rectangular prism, a dome, a cone, a triangular spear, a cube, a pyramid, an elliptical sphere, and a circular sphere.

13. The fluid management device of claim 1, wherein the porous absorption element is fixably coupled to the portion of the length of the flexible tube via at least one of a press fit, an adhesive, stitching, and a mechanical bond.

14. The fluid management device of claim 1, wherein the porous absorption element comprises an antithrombotic material.

15. A fluid management system for controlling fluid at a surgical site, the fluid management system comprising:
   a vacuum source configured to aspirate fluid from the surgical site, wherein the vacuum source comprises an aspiration tube directly coupled thereto such that the vacuum source provides continuous suction through the aspiration tube;
   a dual flow adapter having a main port, a first branch, and a second branch, wherein the first branch is disposed at an acute angle relative to the main port and is coupled directly to the aspiration tube, and wherein the second branch is coaxial with the main port and is configured to be interchangeably coupled to one of a fluid source and an intermittent aspiration adapter configured to provide intermittent fluid aspiration through the flexible tube; and a fluid management device coupled to the main port, the fluid management device comprising:
- a flexible tube having a distal end, a proximal end, and a length therebetween, wherein the length extends along a longitudinal axis, and wherein the distal end comprises a distal opening configured to communicate fluid to and from the surgical site; and
- an absorption element secured to a portion of the length of the flexible tube, wherein the absorption element encloses the distal end.

16. The fluid management system of claim 15, further comprising a continuous aspiration adapter coupled to each of the vacuum source and the aspiration tube, wherein the continuous aspiration adapter includes an elongate body having a first end, a second end, and a center between the first end and the second end, the continuous aspiration adapter increasing in diameter from the first end and the second end toward the center such that the diameter of the continuous aspiration adapter tapers from its center toward the first end and the second end, wherein the second end of the continuous aspiration adapter is coupled directly to the vacuum source.

17. The fluid management system of claim 15, wherein the intermittent aspiration adapter includes an elongate body having an interior surface for fluid communication, a first end, a second end, a middle section, and a center on the middle section, the intermittent aspiration adapter increasing in diameter from the first end and the second end toward the middle section such that the diameter of the intermittent aspiration adapter tapers from the middle section toward the first end and the second end, the middle section including a uniform cross-sectional diameter and a valve extending orthogonally outwardly therefrom, the valve in fluid communication with the interior surface and including a distal end having an opening for selectively occluding to provide a controlled intermittent vacuum force and intermittent aspiration to the surgical site, wherein the second end of the intermittent aspiration adapter is coupled to the vacuum source.

18. The fluid management device of claim 15, wherein the intermittent aspiration adapter comprises an interior surface for fluid communication, a first end, a second end, a middle section, and a center on the middle section, the intermittent aspiration adapter extending from the first end to the second end along the longitudinal axis and increasing in diameter from the first end and the second end toward the middle section such that the diameter of the intermittent aspiration adapter tapers from the middle section toward the first end and the second end, the middle section including a uniform cross-sectional diameter and a funnel valve extending orthogonally outwardly therefrom, the funnel valve in fluid communication with the interior surface and including an opening and a nipple closure, the nipple closure including a nipple configured to selectively occlude the opening to provide a controlled intermittent vacuum force and intermittent aspiration to a surgical site.

19. The fluid management system of claim 15, wherein the second branch comprises a cross-sectional diameter greater than the first branch.

20. The fluid management system of claim 15, further comprising the fluid source, wherein the fluid source is configured to deliver fluid to the surgical site and wherein the fluid source comprises one of fluid-filled bag and a syringe.

21. The fluid management system of claim 15, further comprising an end manifold coupled to the distal end of the flexible tube, wherein the end manifold comprises a plurality of perforations configured to receive a flow of fluid therethrough, wherein the absorption element encloses the end manifold.

* * * * *